United States Patent [19]

Kulagowski et al.

[11] Patent Number: 5,563,152

[45] Date of Patent: Oct. 8, 1996

[54] PYRROLO-PYRIDINE DERIVATIVES

[75] Inventors: Janusz J. Kulagowski, Bishops Stortford; Paul D. Leeson, Cambridge, both of England

[73] Assignee: Merck, Sharp & Dohme Ltd., Hoddesdon, England

[21] Appl. No.: 512,973

[22] Filed: Aug. 9, 1995

[30] Foreign Application Priority Data

Aug. 10, 1994 [GB] United Kingdom .................. 9416189

[51] Int. Cl.$^6$ ........................ A61K 31/435; C07D 471/04
[52] U.S. Cl. ............................ 514/300; 546/113
[58] Field of Search ............................ 546/113; 514/300

[56] References Cited

FOREIGN PATENT DOCUMENTS

| 2044254 | 1/1980 | United Kingdom . |
|---|---|---|
| WO94/20459 | 2/1995 | WIPO . |

*Primary Examiner*—Bernard Dentz
*Attorney, Agent, or Firm*—Robert J. North; Melvin Winokur

[57] ABSTRACT

A class of chemical compounds comprising a pyrrolo[2,3-b]pyridine moiety and a carboxamido-substituted heterocyclic moiety, linked via the 3-position of the pyrrolo[2,3-b] pyridine moiety by a methylene group, are ligands for dopamine receptor subtypes within the body and are therefore useful in the treatment and/or prevention of disorders of the dopamine system, in particular schizophrenia.

7 Claims, No Drawings

PYRROLO-PYRIDINE DERIVATIVES

This invention relates to a particular class of heteroaromatic compounds. More particularly, the invention is concerned with substituted pyrrolo[2,3-b]pyridine derivatives which are ligands for dopamine receptor subtypes within the body, in particular the $D_4$ receptor subtype. They are therefore of use in the treatment and/or prevention of disorders of the dopamine system, including schizophrenia, depression, anxiety, nausea, Parkinson's disease, tardive dyskinesias and extrapyramidal side-effects associated with treatment by conventional neuroleptic agents, neuroleptic malignant syndrome, disorders of hypothalamic-pituitary function such as hyperprolactinaemia and amenorrhoea, and delusional disorders (cf. Catalano et al., *Biol. Psychiatry*, 1993, 34, 459).

Upper gastrointestinal tract motility is believed to be under the control of the dopamine system. The compounds according to the present invention may thus be of use in the prevention and/or treatment of gastrointestinal disorders, and the facilitation of gastric emptying.

Dependence-inducing agents such as cocaine and amphetamine have been shown to interact with the dopamine system. Compounds capable of counteracting this effect, including the compounds in accordance with the present invention, may accordingly be of value in the prevention or reduction of dependence on a dependence-inducing agent.

Dopamine is known to be a peripheral vasodilator; for example, it has been shown to exert a dilatory effect on the renal vascular bed. This implies that the compounds of the present invention may be beneficial in controlling vascular blood flow.

The localisation of dopamine receptor mRNA in rat heart and large vessels has been noted. This suggests a role for dopamine receptor ligands in controlling cardiovascular function, either by affecting cardiac and smooth muscle contractility or by modulating the secretion of vasoactive substances. The compounds according to the present invention may therefore be of assistance in the prevention and/or treatment of such conditions as hypertension and congestive heart failure.

By virtue of their activity as ligands for dopamine receptor subtypes within the body, the compounds in accordance with the present invention may also be of benefit in enhancing cognitive function, and in treating and/or preventing cognitive disorders including presenile and senile dementia (also known as Alzheimer's disease and senile dementia of the Alzheimer type respectively).

Molecular biological techniques have revealed the existence of several subtypes of the dopamine receptor. The dopamine $D_1$ receptor subtype has been shown to occur in at least two discrete forms. Two forms of the $D_2$ receptor subtype, and at least one form of the $D_3$ receptor subtype, have also been discovered. More recently, the $D_4$ (Van Tol et al., *Nature* (London), 1991, 350, 610) and $D_5$ (Sunahara et al., *Nature* (London), 1991, 350, 614) receptor subtypes have been described.

The disclosure of GB-A-2044254 generically encompasses inter alia a class of 3-[piperidin-1-ylalkyl]-1H-pyrrolo[2,3-b]pyridine derivatives substituted on the piperidine ring by an isoindoledione or like moiety. These compounds are alleged therein to be useful as antidepressants. There is, however, no specific disclosure in GB-A-2044254 of a substituted pyrrolo[2,3-b]pyridine derivative, nor indeed any suggestion that such compounds would be of benefit in the treatment and/or prevention of disorders of the dopamine system.

WO-A-94/20459, published on 15 Sep. 1994, describes a class of pyrrolo[2,3-b]pyridine derivatives substituted at the 3-position by inter alia a tetrahydropyridin-1-ylmethyl moiety. There is, however, no disclosure therein of compounds wherein the tetrahydropyridine ring is in turn substituted at the 4-position by a substituted carboxamido moiety.

The compounds in accordance with the present invention, being ligands for dopamine receptor subtypes within the body, in particular the $D_4$ receptor subtype, are accordingly of use in the treatment and/or prevention of disorders of the dopamine system.

The present invention provides a compound of formula I, or a salt or prodrug thereof:

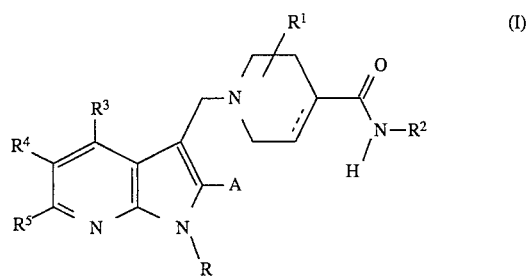

wherein the broken line represents an optional chemical bond;

A represents hydrogen, $C_{1-6}$ alkyl, $C_{1-6}$ alkoxy, halogen, cyano or trifluoromethyl;

R represents hydrogen or $C_{1-6}$ alkyl;

$R^1$ represents hydrogen, halogen, or an optionally substituted $C_{1-6}$ alkyl, $C_{1-6}$ alkoxy, $C_{2-6}$ alkenyl, $C_{2-6}$ alkynyl, aryl, aryl($C_{1-6}$)alkyl, aryl($C_{1-6}$)alkoxy, aryl($C_{2-6}$)alkenyl, aryl($C_{2-6}$)alkynyl, $C_{3-7}$ heterocycloalkyl($C_{1-6}$)alkyl, heteroaryl, heteroaryl($C_{1-6}$)alkyl, heteroaryl($C_{2-6}$)alkenyl or heteroaryl($C_{2-6}$)alkynyl group;

$R^2$ represents an optionally substituted $C_{1-6}$ alkyl, $C_{2-6}$ alkenyl, $C_{2-6}$ alkynyl, aryl, aryl($C_{1-6}$)alkyl, aryloxy($C_{1-6}$)alkyl, aryl($C_{2-6}$)alkenyl, aryl($C_{2-6}$)alkynyl, $C_{3-7}$ heterocycloalkyl($C_{1-6}$)alkyl, heteroaryl, heteroaryl($C_{1-6}$)alkyl, heteroaryl($C_{2-6}$)alkenyl or heteroaryl($C_{2-6}$)akynyl group;

$R^3$, $R^4$ and $R^5$ independently represent hydrogen, hydrocarbon, a heterocyclic group, halogen, cyano, trifluoromethyl, nitro, $-OR^a$, $-SR^a$, $-SOR^a$, $-SO_2R^a$, $-SO_2NR^aR^b$, $-NR^aR^b$, $-NR^aCOR^b$, $-NR^aCO_2R^b$, $-COR^a$, $-CO_2R^a$ or $-CONR^aR^b$; and $R^a$ and $R^b$ independently represent hydrogen, hydrocarbon or a heterocyclic group.

The present invention also provides compounds of formula I above, and salts and prodrugs thereof, wherein A represents hydrogen; and R, $R^1$, $R^2$, $R^3$, $R^4$ and $R^5$ are as defined above.

For use in medicine, the salts of the compounds of formula I will be pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, fumaric acid, maleic acid, succinic acid, acetic acid, benzoic acid, oxalic acid, citric acid, tartaric acid, carbonic acid or phosphoric acid. Furthermore, where the compounds of the invention carry an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands, e.g. quaternary ammonium salts.

The term "hydrocarbon" as used herein includes straight-chained, branched and cyclic groups containing up to 18 carbon atoms, suitably up to 15 carbon atoms, and conveniently up to 12 carbon atoms. Suitable hydrocarbon groups include $C_{1-6}$ alkyl, $C_{2-6}$ alkenyl, $C_{2-6}$ alkynyl, $C_{3-7}$ cycloalkyl, $C_{3-7}$ cycloalkyl($C_{1-6}$)alkyl, aryl, aryl($C_{1-6}$)alkyl, aryl($C_{2-6}$)alkenyl and aryl($C_{2-6}$)alkynyl.

The expression "a heterocyclic group" as used herein includes cyclic groups containing up to 18 carbon atoms and at least one heteroatom preferably selected from oxygen, nitrogen and sulphur. The heterocyclic group suitably contains up to 15 carbon atoms and conveniently up to 12 carbon atoms, and is preferably linked through carbon. Examples of suitable heterocyclic groups include $C_{3-7}$ heterocycloalkyl, $C_{3-7}$ heterocycloalkyl($C_{1-6}$)alkyl, heteroaryl, heteroaryl($C_{1-6}$)alkyl, heteroaryl($C_{2-6}$)alkenyl and heteroaryl($C_{2-6}$)alkynyl groups.

Suitable alkyl groups within the scope of the term "hydrocarbon" and within the definition of the substituents A, R, $R^1$ and $R^2$ include straight-chained and branched alkyl groups containing from 1 to 6 carbon atoms. Typical examples include methyl and ethyl groups, and straight-chained or branched propyl and butyl groups. Particular alkyl groups are methyl, ethyl, n-propyl, isopropyl and t-butyl.

Suitable alkenyl groups within the scope of the term "hydrocarbon" and within the definition of the substituents $R^1$ and $R^2$ include straight-chained and branched alkenyl groups containing from 2 to 6 carbon atoms. Typical examples include vinyl and allyl groups.

Suitable alkynyl groups within the scope of the term "hydrocarbon" and within the definition of the substituents $R^1$ and $R^2$ include straight-chained and branched alkynyl groups containing from 2 to 6 carbon atoms. Typical examples include ethynyl and propargyl groups.

Suitable cycloalkyl groups include groups containing from 3 to 7 carbon atoms. Particular cycloalkyl groups are cyclopropyl and cyclohexyl.

Particular aryl groups within the scope of the term "hydrocarbon" and within the definition of the substituents $R^1$ and $R^2$ include phenyl and naphthyl.

Particular aryl($C_{1-6}$)alkyl groups within the scope of the term "hydrocarbon" and within the definition of the substituents $R^1$ and $R^2$ include benzyl, naphthylmethyl, phenethyl and phenylpropyl.

A particular aryl($C_{2-6}$)alkenyl group within the scope of the term "hydrocarbon" and within the definition of the substituents $R^1$ and $R^2$ is phenylethenyl.

A particular aryl($C_{2-6}$)alkynyl group within the scope of the term "hydrocarbon" and within the definition of the substituents $R^1$ and $R^2$ is phenylethynyl.

Suitable heterocycloalkyl groups include azetidinyl, pyrrolidyl, piperidyl, piperazinyl, morpholinyl and tetrahydrofuryl groups.

A particular $C_{3-7}$ heterocycloalkyl($C_{1-6}$)alkyl group within the scope of the expression "a heterocyclic group" and within the definition of the substituents $R^1$ and $R^2$ is tetrahydrofurylethyl.

Suitable heteroaryl groups within the scope of the expression "a heterocyclic group" and within the definition of the substituents $R^1$ and $R^2$ include pyridyl, quinolyl, isoquinolyl, pyridazinyl, pyrimidinyl, pyrazinyl, pyranyl, furyl, benzofuryl, dibenzofuryl, thienyl, benzthienyl, indolyl, indazolyl, imidazolyl, benzimidazolyl, oxadiazolyl and thiadiazolyl groups.

Particular heteroaryl($C_{1-6}$)alkyl groups within the scope of the expression "a heterocyclic group" and within the definition of the substituents $R^1$ and $R^2$ include thienylmethyl, pyridylmethyl, pyrimidinylmethyl, pyrazinylmethyl and furylethyl.

Particular heteroaryl($C_{2-6}$)alkenyl groups within the scope of the term "hydrocarbon" and within the definition of the substituents $R^1$ and $R^2$ include furylethenyl and thienylethenyl.

The hydrocarbon and heterocyclic groups, as well as the substituents $R^1$ and $R^2$, may in turn be optionally substituted by one or more groups selected from $C_{1-6}$ alkyl, adamantyl, phenyl, aryl($C_{1-6}$)alkyl, halogen, $C_{1-6}$ haloalkyl, $C_{1-6}$ aminoalkyl, trifluoromethyl, hydroxy, $C_{1-6}$ alkoxy, aryloxy, keto, $C_{1-3}$ alkylenedioxy, nitro, cyano, carboxy, $C_{2-6}$ alkoxycarbonyl, $C_{2-6}$ alkoxycarbonyl($C_{1-6}$)alkyl, $C_{2-6}$ alkylcarbonyloxy, arylcarbonyloxy, $C_{2-6}$ alkylcarbonyl, arylcarbonyl, $C_{1-6}$ alkylthio, $C_{1-6}$ alkylsulphinyl, $C_{1-6}$ alkylsulphonyl, arylsulphonyl, trifluoromethanesulphonyloxy, $-NR^vR^w$, $-NR^vCOR^w$, $-NR^vCO_2R^w$, $-NR^vSO_2R^w$, $-CH_2NR^vSO_2R^w$, $-NHCONR^vR^w$, $-PO(OR^v)(OR^w)$, $-CONR^vR^w$, $-SO_2NR^vR^w$ and $-CH_2SO_2NR^vR^w$, in which $R^v$ and $R^w$ independently represent hydrogen, $C_{1-6}$ alkyl, aryl or aryl($C_{1-6}$)alkyl.

The term "halogen" as used herein includes fluorine, chlorine, bromine and iodine, especially fluorine and chlorine.

The present invention includes within its scope prodrugs of the compounds of formula I above. In general, such prodrugs will be functional derivatives of the compounds of formula I which are readily convertible in vivo into the required compound of formula I. Conventional procedures for the selection and preparation of suitable prodrug derivatives are described, for example, in *Design of Prodrugs*, ed. H. Bundgaard, Elsevier, 1985.

Where the compounds according to the invention have at least one asymmetric centre, they may accordingly exist as enantiomers. Where the compounds according to the invention possess two or more asymmetric centres, they may additionally exist as diastereoisomers. It is to be understood that all such isomers and mixtures thereof in any proportion are encompassed within the scope of the present invention.

Suitably, the substituent A represents hydrogen or $C_{1-6}$ alkyl, particularly hydrogen or methyl, and especially hydrogen.

Suitably, the substituent R represents hydrogen or methyl, especially hydrogen.

Suitably, the substituent $R^1$ represents hydrogen, chloro or fluoro, especially hydrogen.

Suitable values for the substituent $R^2$ include $C_{1-6}$ alkyl, aryl, aryl($C_{1-6}$)alkyl, aryloxy($C_{1-6}$)alkyl, aryl($C_{2-6}$)alkenyl, aryl($C_{2-6}$)alkynyl, $C_{3-7}$ heterocycloalkyl($C_{1-6}$)alkyl, heteroaryl, heteroaryl($C_{1-6}$)alkyl or heteroaryl($C_{2-6}$)alkenyl, any of which groups may be optionally substituted. Examples of optional substituents on the group $R^2$ include $C_{1-6}$ alkyl, halogen, nitro, $C_{1-6}$ alkoxy, aryloxy and arylcarbonyloxy.

Particular values of $R^2$ include methyl, benzoyloxy-methyl, ethyl, n-propyl, isopropyl, phenyl, chlorophenyl, ethylphenyl, methoxyphenyl, nitrophenyl, naphthyl, benzyl, chlorobenzyl, phenethyl, phenoxy-methyl, phenylethenyl, chloro-phenylethenyl, methoxy-phenylethenyl, phenylethynyl, tetrahydrofuryl-ethyl, indolyl, benzofuryl, benzthienyl, furylethyl, methyl-furylethyl, thienylethenyl and methyl-furylethenyl.

Suitable values for the substituents $R^3$, $R^4$ and $R^5$ include hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy and $C_{2-6}$ alkylcarbonyl. Particular values include hydrogen, fluoro, chloro, methyl, methoxy and benzyloxy.

One sub-class of compounds according to the invention is represented by the compounds of formula IIA, and salts and prodrugs thereof:

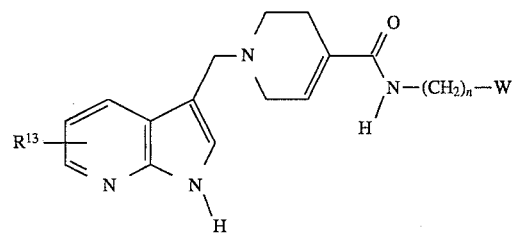

wherein n is zero, 1, 2 or 3;

W represents a group of formula (i), (ii), (iii), (iv), (v) or (vi):

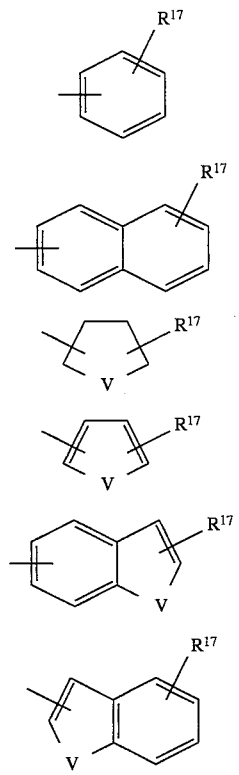

in which V represents oxygen, sulphur, NH or N-methyl; and $R^{13}$ and $R^{17}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{2-6}$ alkylcarbonyl.

Suitably, n is zero or 1, especially zero.

Particular values of $R^{13}$ include hydrogen, fluoro, chloro, methyl, ethyl, methoxy and benzyloxy.

Particular values of $R^{17}$ include hydrogen, chloro, methyl, methoxy and nitro.

A particular subset of the compounds of formula IIA as defined above is represented by the compounds of formula IIB, and salts and prodrugs thereof:

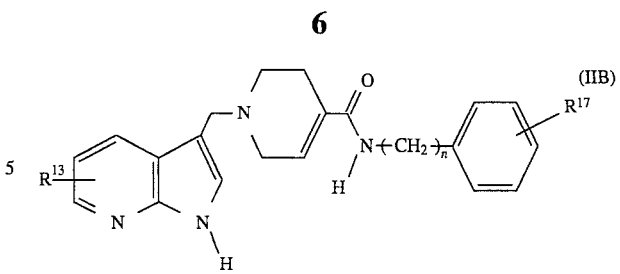

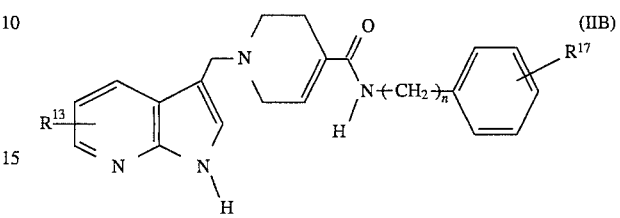

wherein n, $R^{13}$ and $R^{17}$ are as defined with reference to formula IIA above.

In a particular embodiment of the compounds of formula IIB, $R^{13}$ and $R^{17}$ are both hydrogen.

Specific compounds within the scope of the present invention include: 1-(1H-pyrrolo[2,3-b]pyridin-3-ylm-ethyl)-1,2,3,6-tetrahydropyridine-4-carboxylic acid phenylamide; and salts and prodrugs thereof.

The invention also provides pharmaceutical compositions comprising one or more compounds of this invention in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral, parenteral, intranasal, sublingual or rectal administration, or for administration by inhalation or insufflation. Alternatively, the compositions may be presented in a form suitable for once-weekly or once-monthly administration; for example, an insoluble salt of the active compound, such as the decanoate salt, may be adapted to provide a depot preparation for intramuscular injection. An erodible polymer containing the active ingredient may be envisaged. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. Favoured unit dosage forms contain from 1 to 100 mg, for example 1, 2, 5, 10, 25, 50 or 100 mg, of the active ingredient. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

In the treatment of schizophrenia, a suitable dosage level is about 0.01 to 250 mg/kg per day, preferably about 0.05 to 100 mg/kg per day, and especially about 0.05 to 5 mg/kg per day. The compounds may be administered on a regimen of 1 to 4 times per day.

In order to alleviate the symptoms of schizophrenia without causing sedation or extrapyramidal side-effects, it is believed that the dosage level of the active ingredient should be selected such that the dose administered is effective in substantially completely blocking the dopamine $D_4$ receptor subtype in human brain whilst displaying no or negligible $D_2$ receptor subtype occupancy. A suitable dosage level in this regard is about 0.001 to 5.0 mg/kg per day, more particularly about 0.005 to 1.0 mg/kg per day, and especially about 0.01 to 0.5 mg/kg per day.

If desired, the compounds in accordance with this invention may be co-administered with another medicament, for example a known anti-schizophrenic agent which produces its effects via dopamine $D_2$ and/or $5-HT_2$ receptor blockade. Such co-administration may be desirable where a patient is already on an established treatment regime, for example one involving conventional anti-schizophrenic medications such as haloperidol or chlorpromazine.

The compounds in accordance with the present invention may be prepared by a process which comprises reacting a compound of formula III with a compound of formula IV:

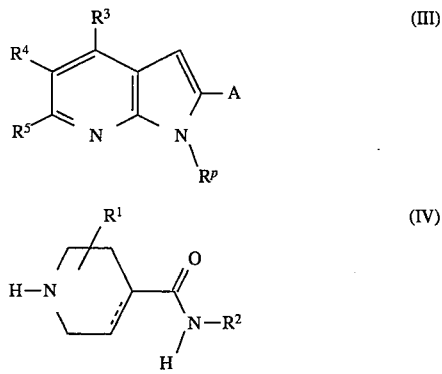

wherein A, $R^1$, $R^2$, $R^3$, $R^4$ and $R^5$ are as defined above, and $R^p$ corresponds to the group R as defined above or represents a suitable protecting group; in the presence of a substantially equimolar amount of formaldehyde; followed, where required, by removal of the protecting group $R^p$; and subsequently, if necessary, N-alkylation by standard methods to introduce the moiety R.

The reaction is conveniently carried out by stirring the reactants in aqueous acetic acid, ideally in the presence of a buffer such as sodium acetate trihydrate, suitably at room temperature.

The formaldehyde may be utilised in the form of paraformaldehyde; or as a solution of formaldehyde in an inert solvent, e.g. 37% aqueous formaldehyde.

The protecting group $R^p$, when present, is suitably an acyl moiety such as acetyl, which can conveniently be removed as necessary by treatment under strongly basic conditions, e.g. sodium methoxide in methanol. Alternatively, the protecting group $R^p$ may be a carbamoyl moiety such as t-butoxycarbonyl (BOC), which can conveniently be removed as necessary by treatment under mildly acidic conditions.

In an alternative procedure, the compounds according to the present invention may be prepared by a process which comprises reacting a compound of formula IV as defined above with a compound of formula V:

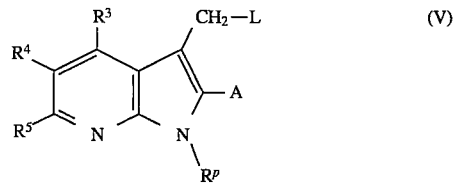

wherein A, $R^3$, $R^4$, $R^5$ and $R^p$ are as defined above, and L represents a suitable leaving group; followed, where required, by removal of the protecting group $R^p$; and subsequently, if necessary, N-alkylation by standard methods to introduce the moiety R.

The leaving group L is suitably a halogen atom, e.g. chlorine or bromine; or a dialkylamino group, e.g. dimethylamino.

When L represents a halogen atom, the reaction between compounds IV and V is conveniently carried out by stirring the reactants under basic conditions in a suitable solvent, for example potassium protecting group $R^p$; and subsequently, if necessary, N-alkylation by standard methods to introduce the moiety R.

The leaving group L is suitably a halogen atom, e.g. chlorine or bromine; or a dialkylamino group, e.g. dimethylamino.

When L represents a halogen atom, the reaction between compounds IV and V is conveniently carried out by stirring the reactants under basic conditions in a suitable solvent, for example potassium carbonate in N,N-dimethylformamide, or triethylamine in tetrahydrofuran or acetonitrile. Where L represents a dialkylamino group, the reaction is conveniently effected by heating the reactants in an inert solvent such as xylene or toluene, typically at the reflux temperature of the solvent.

Where they are not commercially available, the starting materials of formula III, IV and V may be prepared by procedures analogous to those described in the accompanying Example, or by standard methods well known from the art.

It will be appreciated that any compound of formula I initially obtained from any of the above processes may, where appropriate, subsequently be elaborated into a further desired compound of formula I using techniques known from the art. For example, a compound of formula I wherein R is hydrogen initially obtained may be converted into a compound of formula I wherein R represents $C_{1-6}$ alkyl by standard alkylation techniques, such as by treatment with an alkyl iodide, e.g. methyl iodide, typically under basic conditions, e.g. sodium hydride in dimethylformamide, or triethylamine in acetonitrile.

Where the above-described processes for the preparation of the compounds according to the invention give rise to mixtures of stereoisomers, these isomers may be separated by conventional techniques such as preparative chromatography. The compounds may be prepared in racemic form, or individual enantiomers may be prepared either by enantiospecific synthesis or by resolution. The compounds may, for amides, followed by chromatographic separation and removal of the chiral auxiliary.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 1991. The protecting groups may be removed at a convenient subsequent stage using methods known from the art.

The following Example illustrates the preparation of compounds according to the invention.

The compounds useful in this invention potently inhibit [$^3$H]-spiperone binding to human dopamine $D_4$ receptor subtypes expressed in clonal cell lines.

[$^3$H]-Spiperone Binding Studies

Clonal cell lines expressing the human dopamine $D_4$ receptor subtype were harvested in PBS and then lysed in 10 mM Tris-HCl pH 7.4 buffer containing 5 mM $MgSO_4$ for 20 min on ice. Membranes were centrifuged at 50,000g for 15 min at 4° C. and the resulting pellets resuspended in assay buffer (50 mM Tris-HCl pH 7.4 containing 5 mM EDTA, 1.5 mM $CaCl_2$, 5 mM $MgCl_2$, 5 mM KCl, 120 mM NaCl, and 0.1% ascorbic acid) at 20 mg/ml wet weight. Incubations were carried out for 60 min at room temperature (22° C.) in the presence of 0.05–2 nM [$^3$H]-spiperone or 0.2 nM for displacement studies and were initiated by addition of 20–100 μg protein in a final assay volume of 0.5 ml. The incubation was terminated by rapid filtration over GF/B filters presoaked in 0.3% PEI and washed with 10 ml ice-cold 50 mM Tris-HCl, pH 7.4. Specific binding was determined by 10 μM apomorphine and radioactivity determined by counting in a LKB beta counter. Binding parameters were determined by non-linear least squares regression analysis, from which the inhibition constant $K_i$ could be calculated for each test compound.

The compound of the accompanying Example was tested in the above assay, and was found to possess a $K_i$ value for displacement of [$^3$H]-spiperone from the human dopamine $D_4$ receptor subtype of below 1.5 μM.

EXAMPLE 1

1-(1H-Pyrrolo[2,3-b]pyridin-3-ylmethyl)-1,2,3,6-tetrahydropyridine-4-carboxylic acid phenylamide Step 1:
1-Benzyl-1,2,3,6-tetrahydropyridinyl-4-carboxylic acid phenylamide A mixture of pyridine-4-carboxylic acid phenylamide (3.96 g, 20 mmol), benzyl bromide (3.76 g, 22 mmol) and DMF (10 ml) was stirred at 105° C. for 15 h and the resulting solid mass, on cooling, suspended in ethanol (40 ml). Sodium borohydride (0.95 g, 25 mmol) was added in portions and the suspension stirred for 3 h, after which it was filtered, the filtrate evaporated, and the residue partitioned between water (100 ml) and ethyl acetate (2×75 ml). The organic layers were extracted with HCl (1M: 3×50 ml), the combined extracts basified with aqueous sodium hydroxide, and the suspension re-extracted with dichloromethane (2×50 ml). After drying (MgSO$_4$), the dichloromethane layers were evaporated to leave the product as a yellow gum (4.58 g). $\delta_H$ (CDCl$_3$) 2.52 (2H, br s, tetrahydropyridinyl CH$_2$), 2.68 (2H, t, J 5.7 Hz, tetrahydropyridinyl CH$_2$), 3.17 (2H, dd, J 6.0, 2.7 Hz, tetrahydropyridinyl CH$_2$), 3.64 (2H, s, PhC$\underline{H}_2$N), 6.62 (1H, dd, J 3.3, 1.8 Hz, CR=C$\underline{H}$), 7.10 (1H, t, J 7.3 Hz, ArH), 7.26–7.48 (7H, m, ArH) and 7.53 (2H, d, J 7.6 Hz, ArH).

Step 2: 1,2,3,6-Tetrahydropyridinyl-4-carboxylic acid phenylamide, hydrochloride 1-Chloroethyl chloroformate (1.94 ml, 18 mmol) was added to a cooled (ice bath) solution of 1-benzyl-1,2,3,6-tetrahydropyridinyl-4-carboxylic acid phenylamide (4.94 g, 16.6 mmol) in dichloromethane (75 ml), the mixture allowed to warm to room temperature, and stirred for 2 h. The solution was evaporated, the residue redissolved in methanol (50 ml), and the solution stirred at reflux for 0.75 h, after which the solvent was removed. The residue was partitioned between ethyl acetate (50 ml) and water (2×25 ml), the combined aqueous layers washed with ethyl acetate (25 ml) and freeze-dried to leave a yellow foam (4.0 g). $\delta_H$ (D$_2$O) 2.64–2.69 (2H, br s, tetrahydropyridinyl CH$_2$), 3.40 (2H, t, J 6.1 Hz, tetrahydropyridinyl CH$_2$), 3.85–3.88 (2H, m, tetrahydropyridinyl CH$_2$), 6.61 (1H, br s, CR=C$\underline{H}$), 7.22–7.29 (1H, m, ArH) and 7.38–7.52 (4H, m, ArH).

Step 3:
1-(1H-Pyrrolo[2,3-b]pyridin-3-ylmethyl)-1,2,3,6-tetrahydropyridine-4-carboxylic acid phenylamide A solution of the preceding hydrochloride in water was basified with aqueous sodium hydroxide and the resulting suspension extracted with dichloromethane (3×25 ml). The extracts were dried (MgSO$_4$), evaporated and the residual gum (2.16 g) was combined with 3-dimethylaminomethyl-1H-pyrrolo[2,3-b]pyridine (1.75 g, 10 mmol) in xylene (50 ml) and the mixture stirred at reflux for 3.5 h. After decanting the mixture whilst hot, the supernatant was allowed to cool and the solid deposited collected and recrystallised twice from ethanol to leave the title compound as buff plates (0.21 g), m.p. 217°–220°; (Found C, 72.09; H, 5.98; N, 16.59. C$_{20}$H$_{20}$N$_4$O requires C, 72.27; H, 6.06; N, 16.86%); $\delta_H$ (DMSO-d$_6$) 2.36 (2H, br s, tetrahydropyridinyl CH$_2$), 2.59 (2H, t, J 5.6 Hz, tetrahydropyridinyl CH$_2$), 3.11 (2H, br s, tetrahydropyridinyl CH$_2$), 3.75 (2H, s, ArC$\underline{H}_2$N), 6.60 (1H, br s, CR=C$\underline{H}$), 7.00–7.06 (2H, m, ArH & 5-H), 7.28 (2H, t, J 8.3 Hz, ArH), 7.39 (1H, d, J 2.3 Hz, 2-H), 7.64 (2H, dd, J 8.6, 1.0 Hz, ArH), 8.03 (1H, dd, J 7.8, 1.2 Hz, 4-H), 8.20 (1H, dd, J 4.6, 1.5 Hz, 6-H), 9.60 (1H, s, NH), and 11.47 (1H, br s, 1-H); M/z (CI$^+$, NH$_3$) 333 (M+1)$^+$.

What is claimed is:

1. A compound of formula I, or a salt or prodrug thereof:

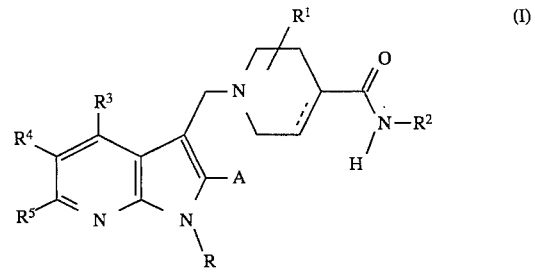

wherein the broken line represents an optional chemical bond;

A represents hydrogen, C$_{1-6}$ alkyl, C$_{1-6}$ alkoxy, halogen, cyano or trifluoromethyl;

R represents hydrogen or C$_{1-6}$ alkyl;

R$^1$ represents hydrogen, halogen, or an optionally substituted C$_{1-6}$ alkyl, C$_{1-6}$ alkoxy, C$_{2-6}$ alkenyl, C$_{2-6}$ alkynyl, aryl, aryl(C$_{1-6}$)alkyl, aryl(C$_{1-6}$)alkoxy, aryl(C$_{2-6}$)alkenyl, aryl(C$_{2-6}$)alkynyl, C$_{3-7}$ heterocycloalkyl(C$_{1-6}$)alkyl, heteroaryl, heteroaryl(C$_{1-6}$)alkyl, heteroaryl($C_{2-6}$)alkenyl or heteroaryl($C_{2-6}$)alkynyl group;

$R^2$ represents an optionally substituted $C_{1-6}$ alkyl, $C_{2-6}$ alkenyl, $C_{2-6}$ alkynyl, aryl, aryl($C_{1-6}$)alkyl, aryloxy($C_{1-6}$)alkyl, aryl($C_{2-6}$)alkenyl, aryl($C_{2-6}$)alkynyl, $C_{3-7}$ heterocycloalkyl($C_{1-6}$)alkyl, heteroaryl, heteroaryl($C_{1-6}$)alkyl, heteroaryl($C_{2-6}$)alkenyl or heteroaryl($C_{2-6}$)alkynyl group;

$R^3$, $R^4$ and $R^5$ independently represent hydrogen, hydrocarbon, a heterocyclic group, halogen, cyano, trifluoromethyl, nitro, —$OR^a$, —$SR^a$, —$SOR^a$, —$SO_2R^a$, —$SO_2NR^aR^b$, —$NR^aR^b$, —$NR^aCOR^b$, —$NR^aCO_2R^b$, —$COR^a$, —$CO_2R^a$ or —$CONR^aR^b$; and $R^a$ and $R^b$ independently represent hydrogen, hydrocarbon or a heterocyclic group.

2. A compound as claimed in claim 1 wherein A represents hydrogen.

3. A compound represented by formula IIA, and salts and prodrugs thereof:

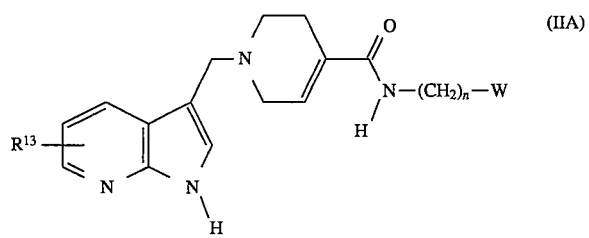

wherein n is zero, 1, 2 or 3;

W represents a group of formula (i), (ii), (iii), (iv), (v) or (vi):

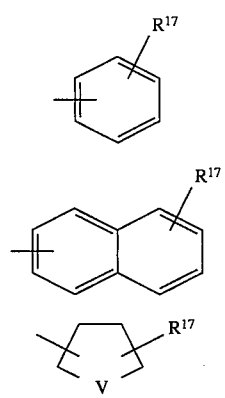

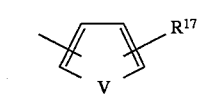

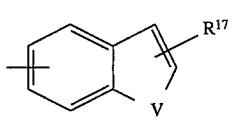

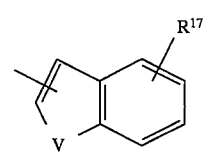

in which V represents oxygen, sulphur, NH or N-methyl; and $R^{13}$ and $R^{17}$ independently represent hydrogen, halogen, cyano, nitro, trifluoromethyl, amino, $C_{1-6}$ alkylamino, di($C_{1-6}$)alkylamino, $C_{1-6}$ alkyl, $C_{1-6}$ alkoxy, aryl($C_{1-6}$)alkoxy or $C_{1-6}$ alkylcarbonyl.

4. A compound as claimed in claim 3 represented by formula IIB, and salts and prodrugs thereof:

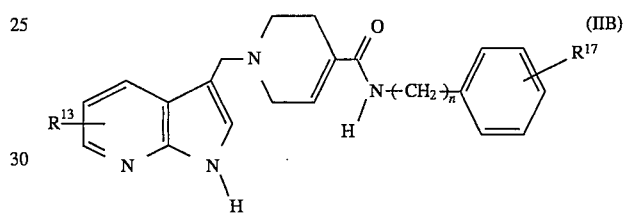

wherein n, $R^{13}$ and $R^{17}$ are as defined in claim 3.

5. A compound as claimed in claim 1 selected from: 1-(1H-pyrrolo[2,3-b]pyridin-3-ylmethyl)-1,2,3,6-tetrahydropyridine-4-carboxylic acid phenylamide; and salts and prodrugs thereof.

6. A pharmaceutical composition comprising a compound of formula I as defined in claim 1, or a pharmaceutically acceptable salt thereof or a prodrug thereof, in association with a pharmaceutically acceptable carrier.

7. A method for the treatment and/or prevention of disorders of the dopamine system, which comprises administering to a patient in need of such treatment an effective amount of a compound of formula I as defined in claim 1, or a pharmaceutically acceptable salt thereof or a prodrug thereof.

* * * * *